United States Patent [19]

Carpenter et al.

[11] 4,084,440
[45] Apr. 18, 1978

[54] CHROMATOGRAPH INJECTION SYSTEM

[75] Inventors: Wilfred C. Carpenter, Ralston; Gary N. Schmitz; Walter J. Fenrick, both of Medicine Hat, all of Canada

[73] Assignee: Her Majesty in Right of Canada as Represented by the Minister of National Defence, Ottawa, Canada

[21] Appl. No.: 729,382

[22] Filed: Oct. 4, 1976

[30] Foreign Application Priority Data

Mar. 31, 1976 Canada .................................. 249316

[51] Int. Cl.² .............................................. G01N 1/22
[52] U.S. Cl. ................................................ 73/422 GC
[58] Field of Search ........................... 73/422 GC, 23.1

[56] References Cited

U.S. PATENT DOCUMENTS

| 3,000,218 | 9/1961 | Marks et al. | 73/422 GC |
|---|---|---|---|
| 3,253,455 | 5/1966 | Ferrin | 73/422 |
| 3,585,863 | 6/1971 | Hrdina | 73/422 GC |
| 3,668,935 | 6/1972 | Coelho | 73/422 GC |
| 3,730,082 | 5/1963 | Penton | 73/422 GC |
| 3,779,066 | 12/1973 | Fore et al. | 73/23.1 |

Primary Examiner—S. Clement Swisher
Attorney, Agent, or Firm—Richard J. Hicks; Stanley E. Johnson

[57] ABSTRACT

A method and apparatus for the rapid transfer of substantially all of a sample adsorbed in a gas sampler tube into a gas or other chromatograph analysis system, in which the chromatograph carrier gas or other fluid is circulated through the chromatograph and a bypass valve in an injection device mounted externally thereof so as to establish equilibrium conditions therein and simultaneously permitting loading of the sampler tube into the injection device without disturbing the fluid flow. The sample is heated and then the fluid flow is diverted through the sampler tube to desorb the sample and carry it directly to the chromatograph column.

20 Claims, 4 Drawing Figures

CHROMATOGRAPH INJECTION SYSTEM

This invention relates to a method and apparatus for introducing substantially all of a sample, usually from a solid phase substrate, contained in a sampler tube into a gas or other chromatograph analysis system. More particularly this invention relates to a temperature controlled chamber and valve system which is adapted to be attached to the inlets of any one of a variety of chromatographic instruments and which permits substantially all of the sample material to be injected into the instrument with substantially no carrier flow disruption and minimal sampler manipulation.

Atmospheric gas sampling is well known and methods for conducting such sampling have become increasingly sophisticated over the years. Sampling is conducted on an increasing scale for many different purposes. Environmentalists are concerned with industrial pollutants such as sulphur dioxide and heavy hydrocarbons, agricultural pollutants such as undesirable concentrations of pesticides, insecticides and herbicides and such other pollutants as deuterium and tritiated water which may escape from nuclear installations. Military and civil authorities may also be concerned with the measurement of relatively low concentrations of chemical warfare (CW) agents such as the so called "nerve gases". Whatever the object of the sampling, the procedure is substantially the same in that field operatives are provided with a pump of known volume and a series of open ended sampler tubes containing an appropriate adsorbent such as a silica gel, activated charcoal, porous polymer or gas chromatograph packing, and instructed to draw a known volume of air through the sampler tubes by the manipulation of their pump the appropriate number of times. Relatively large concentrations of specific pollutants may be determined colorimetrically in the field but relatively low concentrations of other pollutants may well require the more sophisticated techniques which are only available in a properly equipped laboratory for qualitative and quantitative determination. A relatively large number of the sampler tubes, containing the adsorbed materials, are therefore packed in special boxes, known per se, and transported to a laboratory. The laboratory is then faced with the task of analysing large numbers of very small samples, of the order of $1 \times 10^{-9}$ grams, both qualitatively and quantitatively, and it has been found that a most useful tool for this purpose is a commercially available chromatograph. Throughout this specification reference will be made to gas chromatographs although it will be appreciated that the apparatus and techniques described herein may equally well be applicable to liquid chromatographs. The term gas should, therefore, be construed to include other fluids and particularly liquids. Difficulties remain, however, in the rapid and quantitative transfer of the adsorbed sample from the sampler tube to the gas chromatograph, because of the time taken for the transfer to take place and for the chromatograph to reach an equilibrium condition. Indeed, due to the fugitive nature of certain chemicals and the ease with which they decompose under heat, all or some of the sample may be completely lost before it ever reaches the G.C. column. It has been found that rapid transfer of the sample to the G.C. column, in the order of 2-3 seconds as opposed to the prior art time of 2-3 minutes, significantly improves the sensitivity and accuracy of the detector, making it possible to qualitatively and quantitatively identify agents which are present in quantities so low that heretofore they have remained undetected in even relatively sophisticated gas analysis.

It is an object of the present invention to provide a method for the rapid and substantially complete injection of a relatively small sample into a gas chromatograph column with a minimum of carrier gas flow disruption and minimal sampler manipulation.

It is another object of the present invention to provide an apparatus, for attachment to a gas chromatograph apparatus, to facilitate the rapid transfer of a solid or liquid phase sample into the gas chromatograph with a minimum of disruption to the carrier gas flow through G.C. column.

Thus, by one aspect of this invention there is provided an apparatus for rapid quantitative transfer of a sample into a chromatograph, comprising:

(a) a body having inlet and outlet means;

(b) first passage means defining a first fluid flow path between said inlet and said outlet means;

(c) a sample housing removably located within said body and having a sample chamber in series with said first fluid flow path;

(d) second passage means defining a second fluid flow path between said inlet and outlet means which by passes said sample chamber; and (e) valve means for direction of fluid along a selected one of said first and second flow paths.

By another aspect of this invention there is provided a method for rapid quantitative transfer of a sample into a chromatograph comprising the steps;

(a) flowing a fluid through a bypass passage in an injection device and into said chromatograph until substantially equilibrium conditions are attained;

(b) inserting a sample container containing a sample to be tested into an isolated sample chamber in said injection device while continuing said fluid flow through said bypass passage; and (c) diverting said fluid flow from said bypass passage so as to pass through said sample container thereby transferring said sample to said chromatograph without interruption of said fluid flow.

The invention will be described in more detail hereinafter by reference to the accompanying drawings in which.

Figure 1:
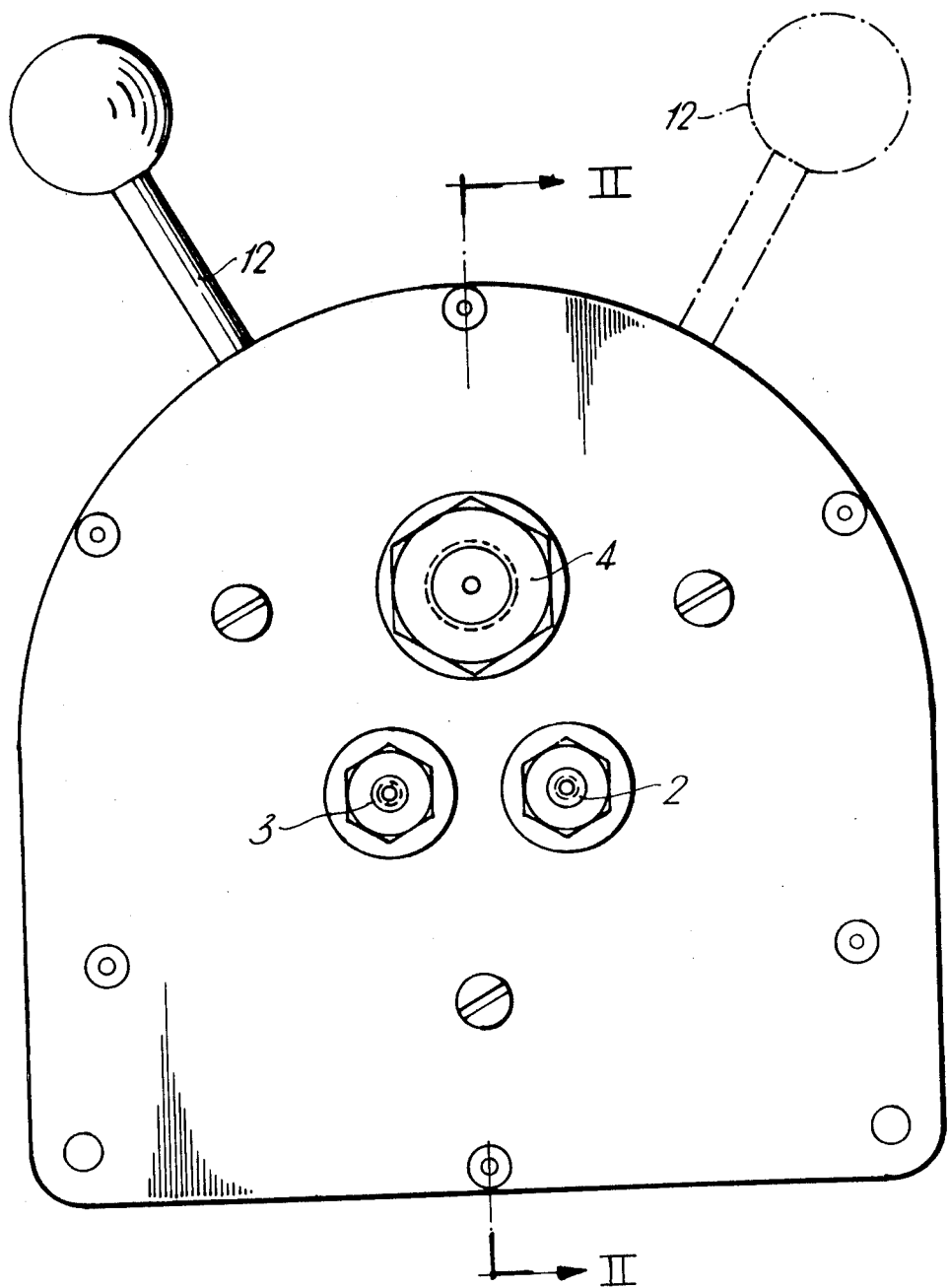
FIG. 1 is a rear view of one embodiment of the injection device of the present invention.
Figure 2:
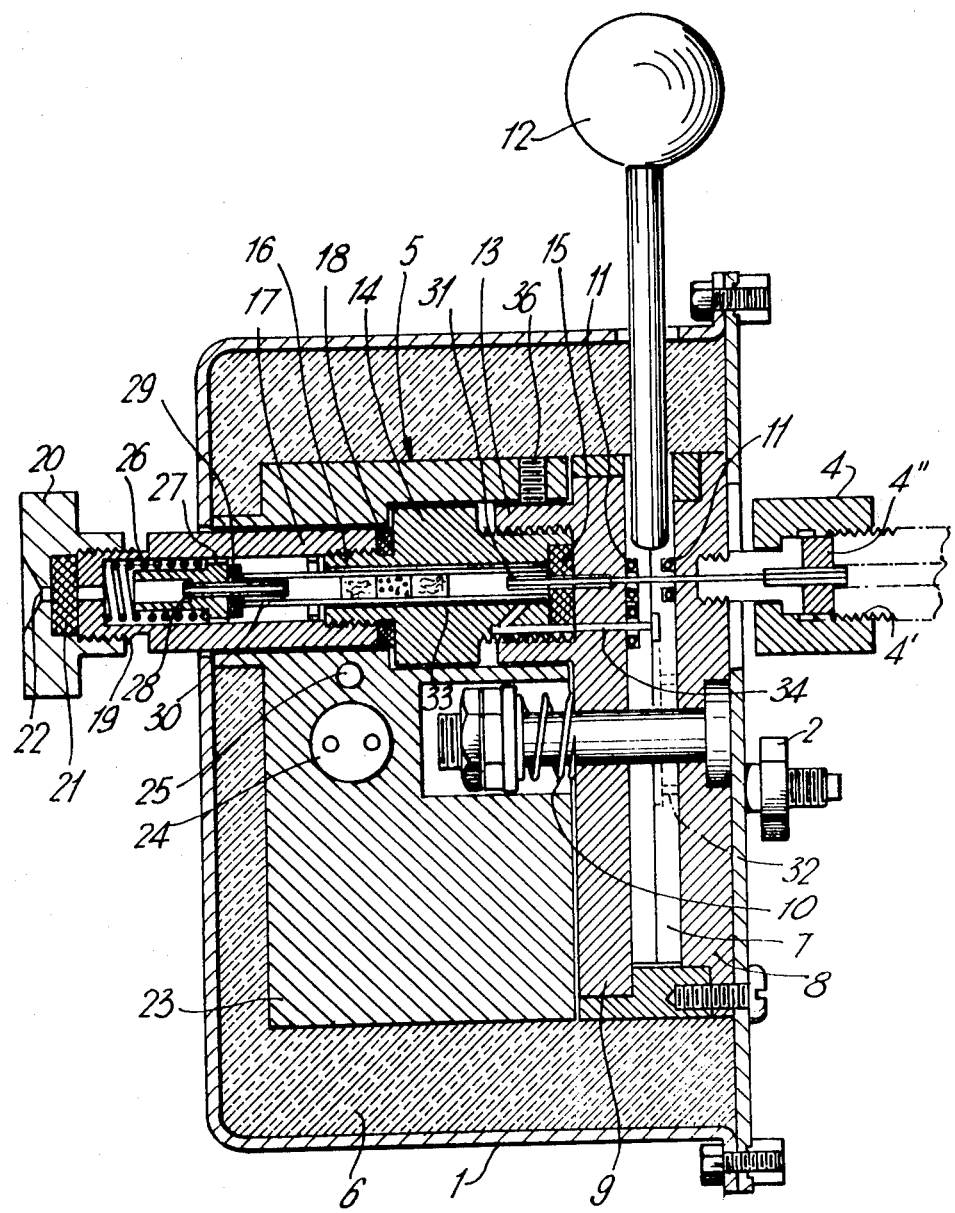
FIG. 2 is a sectional view of the device of FIG. 1 taken along line II—II.

Referring firstly to FIGS. 1 and 2, it will be noted that the injection device of the present invention comprises a temperature controlled chamber and valve system which may be attached directly to the appropriate inlets of various chromatographic instruments. An outer casing 1 encloses the valve system which is provided with a carrier gas inlet port 2, a carrier gas outlet port 3, and a chromatograph inlet port 4 which is suitably adapted for connection to and sealing engagement with the inlet of any standard gas chromatograph device for example by an internal thread 4' and resilient seal 4". The valve device, indicated generally at 5, is contained within the casing 1 and the space therebetween is filled with an insulating medium 6, such as glass fibre wool.

A valve slide 7, provided with a plurality of ports which will be described in more detail hereinafter, is resiliently held between a valve slide base 8 and a valve slide plate 9 by means of a compression spring 10 and sealed by VITON ® "O" rings 11 fitted in the valve slide 7 around each port. The use of heat resistant "O" rings 11 permits sealing with less pressure from spring 10 as well as making the fit between these ports less critical. The surface of the valve slide base 8 and the valve slide plate 9 are ground and lapped to allow the seals to slide with minimum friction when the valve slide lever 12 is moved. Valve slide plate 9 is provided with an internally threaded shoulder portion 13 adapted to receive an inner sample chamber housing 14 in threaded and sealing engagement against a resilient seal 15. Inner sample chamber housing 14 is provided with an externally threaded shoulder portion 16 adapted to receive an outer sample chamber housing 17 in threaded and sealing engagement against a resilient TEFLON ® washer 18. Outer housing 17 is adapted to extend through casing 1 and is provided with an externally threaded end 19, which in turn receives a cap 20 in threaded and sealing engagement against a septum seal 21. Cap 20 is provided with a central bore 22 so as to provide an entry means to the sample chamber for injection of a sample or solvent by syringe in a manner to be described in more detail hereinafter. The inner and outer sample chamber housings 14 and 17 are substantially surrounded by an aluminum or other metal heat sink 23 secured to slide 9 by screw 36 and which can be uniformly heated by any suitable heater such as a thermostatically controlled cartridge heater 24. A hole 25 is provided in heat sink 23 to receive a thermocouple (not shown).

Outer sample chamber housing 17 is provided with a spring loaded hollow plunger 26 having gas orifices 27 at the periphery thereof and a tube 28 and resilient seal 29 adapted to engage a glass sample tube or housing 30 containing the material to be analysed and resiliently urge same against resilient seal 15. Seal 15 is similarly provided with a tube 31 which provides a gas flow path into valve slide plate 9. It will be appreciated that the internal diameter of both the inner and outer sample chamber housings 14 and 17 is somewhat greater than the external diameter of the sample tube 30 so as to provide a chamber 33 and a gas flow path externally of the tube 30.

In operation, the carrier gas used in the valve system is the same as that used in the gas chromatograph and is generally any relatively inert gas such as nitrogen, argon or helium. The carrier gas enters the valve device from the chromatograph through fitting 2 and can then be diverted either through the sampler tube 30 or directly returned to the chromatograph according to the position of the valve slide 7 which is controlled by valve slide lever 12. When the slide lever 12 is in the bypass position (as shown in dotted lines in FIG. 1) the ports of the valve slide 7 are aligned with the fittings 2 and 3 so that the carrier gas flow is from fitting 2 through fitting 3 and into the column of the chromatograph. In this position the carrier gas flows normally through the chromatogrpah while the chamber 33 is isolated from the gas inlet by the valve slide 7. The outer sample housing 17 can now be removed, by unscrewing from shoulder 16, and a sample tube 30 can be inserted into the chamber 33 and located over tube 31.

Outer housing 17 can then be replaced, locating the other end of the tube 30 over tube 28 and thus retaining the sample tube in gas tight relationship to seals 15 and 29. The entire chamber 33, tube 30 and sample contained therein can then be heated by cartridge heater 24 so as to prepare the material to be analysed for desorbtion from the adsorbent material in the sample tube. When the temperature and other conditions reach equilibrium the sample can be injected, in the form of a gas, into the chromatograph. The valve slide lever 12 is moved to the "inject" position, as shown in full in FIG. 1 and in FIG. 2, thereby allowing the ports 32 in valve slide 7 to direct the carrier gas flow from fitting 2 through the valve slide 7 into the chamber 33 via a carrier gas passage 34 in slide plate 9 and inner housing 14 while sealing off flow to fitting 3. The carrier gas then flows through orifices 27 into hollow plunger 26 and hence into the sample tube 30, at a predetermined temperature. On passing through the solid phase in the sample chamber of the sample tube or housing 30 the sample material is desorbed and carried through tube 31 and valve slide 7 into the chromatograph inlet 4.

It will be appreciated that in an alternative procedure, the lever 12 may be held in the "inject" position and the sampler tube 30 replaced with an open glass tube so that the entire valve assembly functions in a manner similar to a conventional chromatograph injection block in that samples may be injected into the open glass tube via a syringe needle which can be inserted through bore 22 and through septum seal 21. It may also be desired to inject reagents or other solvents into the sample tube 30 in a similar manner.

Figure 3:
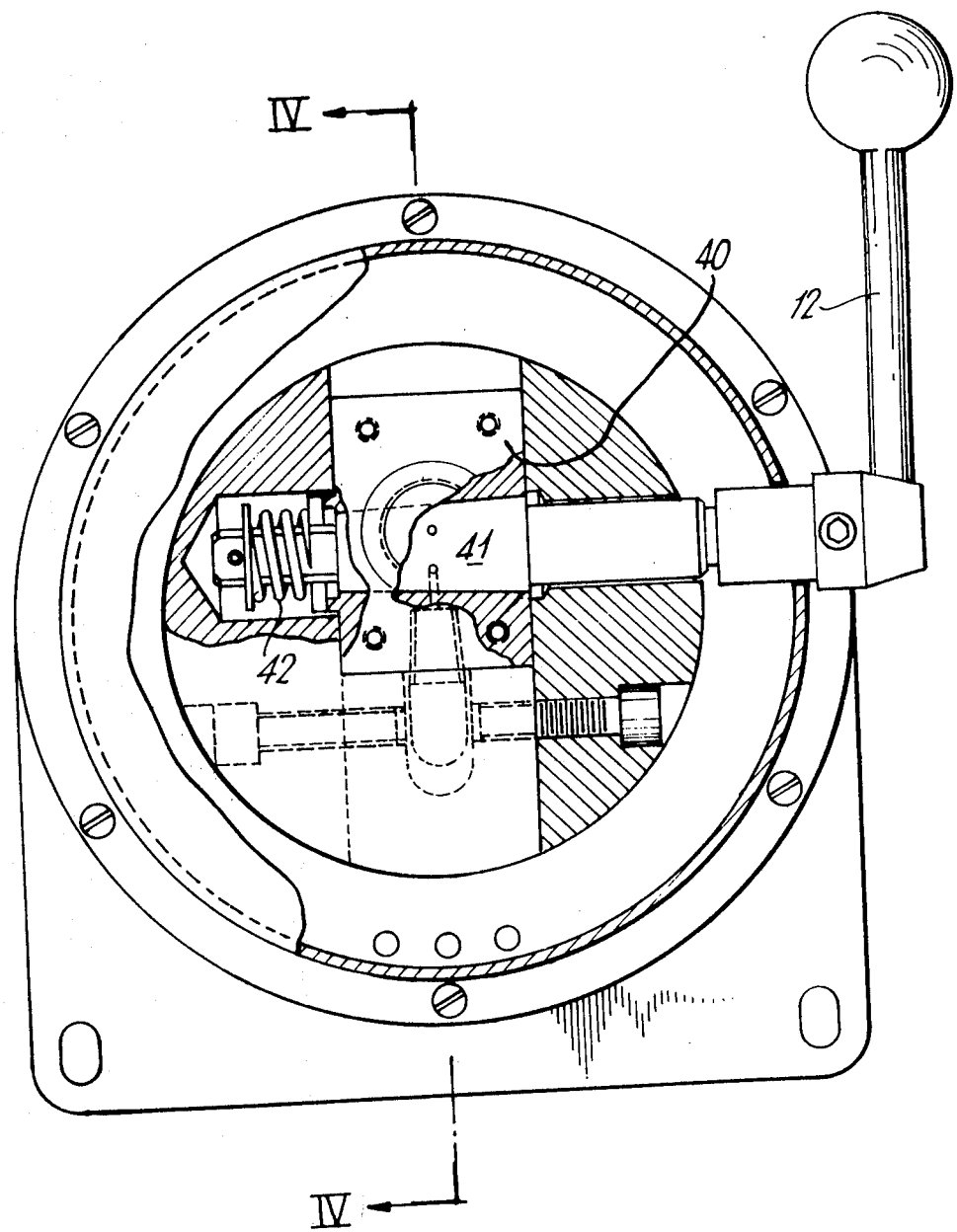
FIG. 3 is a rear view, partly broken away, of an alternative embodiment of the injection device of the present invention.
Figure 4:
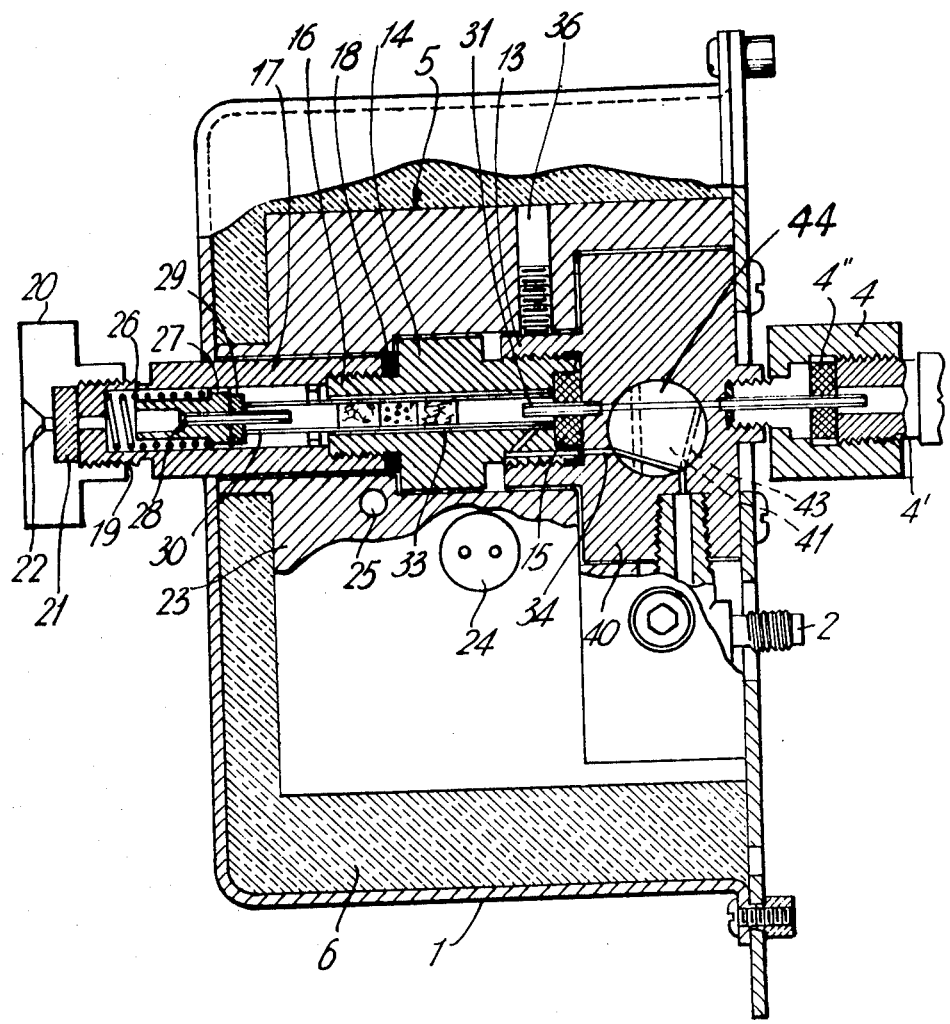
FIG. 4 is a sectional view of the device of FIG. 3 taken along line IV—IV.

Turning now to FIGS. 3 and 4, there is shown an alternative embodiment of this invention in which the slide valve 7 and its associated valve slide base 8, valve slide plate 9 and compression spring 10, are replaced by a tapered rotary valve block 40 and a tepered rotary valve 41. The tapered valve 41 may be fabricated in any suitable material such as stainless or tool steel or a resin material such as VESPEL ® which is a polyimide resin marketed by Dupont. The Vespel may be graphite impregnated to ensure smooth operation. Preferably, but not essentially, block 40 is fabricated in naval bronze.

In operation, the embodiment shown in FIGS. 3 and 4 functions in a precisely similar manner to that hereinbefore described. The valve 41, which is maintained in resilient contact with block 40 by means of a compression spring 42, may be moved by means of lever 12 between a bypass position in which carrier gas enters via inlet port 2 and is directed to the chromatograph port 4 via the bore 43, shown in dashed lines in FIG. 4, thereby bypassing the sample chamber entirely. When the lever 12 is moved to the inject position, the valve 41 is moved clockwise to take up the position shown in solid lines in FIG. 4, that is carrier gas enters the device at port 2 and is directed along bore 43 to gas passage 34 and thence into sample chamber 33. The gas exiting from the sample tube 30 and tube 31 is conveyed along bore 44 to chromatograph inlet 4, for analysis in the G.C. column.

It will be appreciated that many modifications may be made to the apparatus of the present invention without departing from the scope thereof and it will be understood that the invention may be practised in a manner other than that as specifically described herein. The invention is, therefore, only to be construed with reference to the appended claims.

We claim:

1. An apparatus for rapid quantitative transfer of a sample into a chromatograph comprising:
   (a) a body having inlet and outlet means;
   (b) first passage means defining a first fluid flow path between said inlet and said outlet means;
   (c) a sample housing removably located within said body and having a sample chamber in series with said first fluid flow path;
   (d) second passage means defining a second fluid flow path between said inlet and outlet means which bypasses said sample chamber;
   (e) valve means for direction of fluid along a selected one of said first and second flow paths; and
   (f) heating means in said body to thereby ensure substantially equilibrium conditions within said sample housing.

2. An apparatus as claimed in claim 1 wherein said valve means is a tapered rotary valve.

3. An apparatus as claimed in claim 1 wherein said valve means is a slide valve.

4. An apparatus as claimed in claim 1 wherein said sample housing is located in a chamber within said body.

5. An apparatus as claimed in claim 1 wherein said heating means heats a sample contained in said sample chamber.

6. An apparatus as claimed in claim 1 wherein said body includes an insulated heat sink and said heating means is thermostatically controlled.

7. An apparatus as claimed in claim 1 wherein said outlet means is adapted for attachment to a gas chromatograph sample inlet means.

8. An apparatus as claimed in claim 1 wherein said sample housing comprises an open-ended sampler tube.

9. An apparatus as claimed in claim 4 wherein said chamber is detachably secured to said body.

10. An apparatus as claimed in claim 4, wherein said chamber includes an outer section in sealing engagement therewith and which is detachable therefrom so as to facilitate insertion of said sample housing into said chamber.

11. An apparatus as claimed in claim 10 wherein said outer section extends beyond said body and includes an outer detachable cap and seal means.

12. An apparatus as claimed in claim 11 wherein said cap and seal means includes a septum to thereby facilitate needle injection of material into said sample chamber.

13. An apparatus as claimed in claim 1 wherein at least part of said first and second passage means are formed in said valve means.

14. An apparatus as claimed in claim 1 wherein said fluid is a carrier gas for carrying a sample into a gas chromatograph.

15. An apparatus as claimed in claim 1 wherein insertion of said sample housing into said body defines a portion of said first fluid flow path and places the sample chamber in series with said first flow path.

16. A method for rapid quantitative transfer of a sample into a gas chromatograph comprising the steps:
   (a) flowing a carrier gas through a bypass passage in an injection device and into said chromatograph until substantially equilibrium conditions are attained;
   (b) inserting a sample housing containing a sample to be tested into an isolated chamber in said injection device while continuing said gas flow through said bypass; and
   (c) diverting said gas flow from said bypass passage so as to pass through said sample housing thereby desorbing and transferring said sample to said chromatograph without interruption of said gas flow.

17. A method as claimed in claim 16 including the step of heating said sample after insertion into said sample chamber and prior to said diversion of gas through said sample chamber.

18. A method as claimed in claim 17 wherein said sample is adsorbed onto an adsorbent contained in a sampler tube.

19. A method as claimed in claim 16 including the step of injecting a reagent material into said sample chamber.

20. A method as claimed in claim 19 wherein said sample is a solid or liquid contained in a sampler tube.

* * * * *